US012788355B2

(12) United States Patent
Somerkivi

(10) Patent No.: US 12,788,355 B2
(45) Date of Patent: Nov. 10, 2026

(54) TOMOGRAPHIC RADIOGRAPHY AND CALIBRATION

(71) Applicant: PLANMECA OY, Helsinki (FI)

(72) Inventor: Ville Somerkivi, Helsinki (FI)

(73) Assignee: PLANMECA OY, Helsinki (FI)

( * ) Notice: Subject to any disclaimer, the term of this patent is extended or adjusted under 35 U.S.C. 154(b) by 70 days.

(21) Appl. No.: 18/848,417

(22) PCT Filed: Mar. 17, 2023

(86) PCT No.: PCT/FI2023/050156

§ 371 (c)(1),
(2) Date: Sep. 18, 2024

(87) PCT Pub. No.: WO2023/175244

PCT Pub. Date: Sep. 21, 2023

(65) Prior Publication Data

US 2025/0204883 A1 Jun. 26, 2025

(30) Foreign Application Priority Data

Mar. 18, 2022 (FI) ..................................... 20225241

(51) Int. Cl.
*A61B 6/58* (2024.01)
*A61B 6/00* (2024.01)
(Continued)

(52) U.S. Cl.
CPC ................ *A61B 6/585* (2013.01); *A61B 6/02* (2013.01); *A61B 6/4233* (2013.01); *A61B 6/482* (2013.01); *A61B 6/51* (2024.01); *A61B 6/5205* (2013.01); *A61B 6/5258* (2013.01); *A61B 6/582* (2013.01); *A61B 6/025* (2013.01); *A61B 6/4035* (2013.01);
(Continued)

(58) Field of Classification Search
CPC ......... A61B 6/585; A61B 6/02; A61B 6/5258; A61B 6/582
See application file for complete search history.

(56) References Cited

U.S. PATENT DOCUMENTS

| | | | | |
|---|---|---|---|---|
| 2008/0050002 A1 | | 2/2008 | Arnold | |
| 2008/0181367 A1* | | 7/2008 | Heigl ..................... | A61B 6/032 378/207 |

(Continued)

FOREIGN PATENT DOCUMENTS

| | | | |
|---|---|---|---|
| DE | 102006049664 A1 | 5/2008 | |
| EP | 2959836 A1 | 12/2015 | |

(Continued)

OTHER PUBLICATIONS

Finnish Patent Office Search Report for 2022524 dated Oct. 18, 2022.

(Continued)

*Primary Examiner* — Chih-Cheng Kao
(74) *Attorney, Agent, or Firm* — Lippes Mathias LLP

(57) ABSTRACT

This disclosure relates to calibrating tomographic imaging systems, wherein the calibrating comprises a step of generating what could be called a virtual tomographic calibration image. Such image is based on exposing an attenuator object and virtual tomographic calibration images then provide a base for generating calibration functions to be applied to diagnostic tomographic images of an anatomy.

23 Claims, 6 Drawing Sheets

(51) Int. Cl.

| | |
|---|---|
| ***A61B 6/02*** | (2006.01) |
| ***A61B 6/40*** | (2024.01) |
| ***A61B 6/42*** | (2024.01) |
| ***A61B 6/50*** | (2024.01) |
| ***A61B 6/51*** | (2024.01) |

(52) U.S. Cl.

CPC ........... *A61B 6/4241* (2013.01); *A61B 6/4441* (2013.01); *A61B 6/502* (2013.01); *A61B 6/5241* (2013.01); *A61B 6/583* (2013.01)

(56) References Cited

U.S. PATENT DOCUMENTS

2009/0285366 A1* 11/2009 Essenreiter ............ A61B 34/20 378/207
2010/0290680 A1 11/2010 Declerck et al.
2014/0112565 A1 4/2014 Roessl
2015/0305696 A1* 10/2015 Yamakawa .............. A61B 6/51 378/19

FOREIGN PATENT DOCUMENTS

EP 3705047 A1 9/2020
KR 20110040329 A * 4/2011 ............... A61B 6/54
WO 2019162860 A1 8/2019
WO 20210857000 A1 5/2021

OTHER PUBLICATIONS

International Search Report for PCT/FI2023/050156 dated Jul. 29, 2016, 16 pages.
A Neural Network-Based Method for Spectral Distortion Correction in Phton Counting X-ray CT, Touch et al., Physics in Medicine and Biology, vol. 61, No. 16, Jul. 29, 2016.

* cited by examiner

TOMOGRAPHIC RADIOGRAPHY AND CALIBRATION

FIELD OF THE DISCLOSURE

This disclosure relates to tomographic radiography, particularly to calibrating tomographic imaging systems designed to acquire sets of image frames of an anatomy being imaged. The calibration according to this disclosure can be applied, particularly, in the context of dental panoramic imaging and/or of spectral radiography.

BACKGROUND

Medical radiography can be considered to typically include a sort of balancing problem between a radiation dose for which a living organism is reasonable to be exposed and image quality sufficient for being able make a diagnosis.

During the past several decades, progress in radiation detecting technology has been one of the reasons for it having become possible to take diagnostically applicable radiographs by smaller radiation doses. This progress has included going from film era to digital imaging, while there has been advances in the digital imaging technology itself as well.

The more modern detector technologies applied in radiography include so-called direct conversion detectors in which there is no intermediate step of converting X-ray radiation to light prior to detecting and which make possible using smaller radiation doses.

Photon counting detectors can be configured to simultaneously detect photons within more than one energy range, which provides possibilities for e.g. spectral radiography, also called material decomposition, based on just a single exposure by one radiation spectrum.

One of the criteria relating to being able to generate good quality images is a properly calibrated imaging system. For one, during an exposure, mutual locations of physical components of an imaging system may slightly differ from the designed ones and e.g. as far as digital imaging is concerned, individual imaging detectors of the same design and even detector pixels of an individual detector do not necessarily give identical detection signals for a given radiation intensity.

When calibrating an imaging system one may wish to find a correlation in the imaging system between attenuation of radiation in an object and signal values being generated at detector pixels by using calibration objects of known radiation attenuation characteristics and dimensions, placed within the path of the X-ray beam between the X-ray source and detector.

Tomographic imaging can be characterized as being an imaging technology by which one is able to image a volume within an object being imaged without other volumes within the object the X-ray beam penetrates during imaging being visible in the image being generated. Traditionally, tomographic imaging has also been referred to as layer imaging, this referring to the context of various imaging modes designed enabling a desired internal layer of an object becoming visible in an image. One such traditional imaging mode is what has been called dental panoramic imaging, in which the object anatomy is (a part of) cranium and the layer one wishes to get visible is dental arch.

Dental panoramic imaging systems are an example of systems which nowadays are known to apply digital imaging technology based on acquiring, during an imaging scan, a set of 2D image frames, the data of which set is then digitally post-processed to generate the desired tomographic (layer) image.

Dental panoramic imaging is also an example of frame imaging modes in which the imaging process includes acquiring image frames in high frequency while scanning over the object by an X-ray beam. Frame-acquiring rate in dental panoramic imaging may be of the order of 200-300 frames per second while radiation is generated by an X-ray tube current of less than 20 mA. Given these parameter values and high attenuation of the X-ray quantum spectrum when penetrating a skull, a signal to be read out from a detector pixel may be very small—like in the context of using photon counting detectors, the count in a single detector pixel upon a given read-out may approach or even be zero.

More generally, medical radiography typically includes balancing between also other criteria than the radiation dose and image quality discussed above. In the context of scanning exposures, matters to be considered include total duration of the scan, scanning speed, motion artefacts and maximum frame rate the technology used in the imaging system allows for. In view of that, one may wish to have available an imaging system which is capable of coping with low detector pixel signals—like low photon counts or ones with low signal to noise ratio, which then may e.g. allow for using a combination of features higher scanning speed and higher frame rate, and/or may make it possible to use a less powerful X-ray generator.

BRIEF DESCRIPTION

The current disclosure relates to calibration in an imaging context which includes acquiring image frames while an X-ray beam moves over an object, and where a subsequent image processing includes processing information of the frames. One such practical example includes summing frames so as to partially overlap each other, as may be done in the context of dental panoramic imaging. While e.g. in that context one could consider generating calibration data relating to attenuation of radiation in a medium based directly on detector frame pixel signals of a given calibration exposure as such, this disclosure teaches generating first virtual tomographic images from native detector pixel data of individual calibration exposures by processing the detected pixel values of the detector frame the same way as will be done upon actual diagnostic imaging, and using virtual tomographic image data thus generated in generating the actual calibration data.

DESCRIPTION OF FIGURES

The disclosure below will be referring to the attached Figures, out of which

DETAILED DESCRIPTION OF THE FIGURES

Figure 1A:
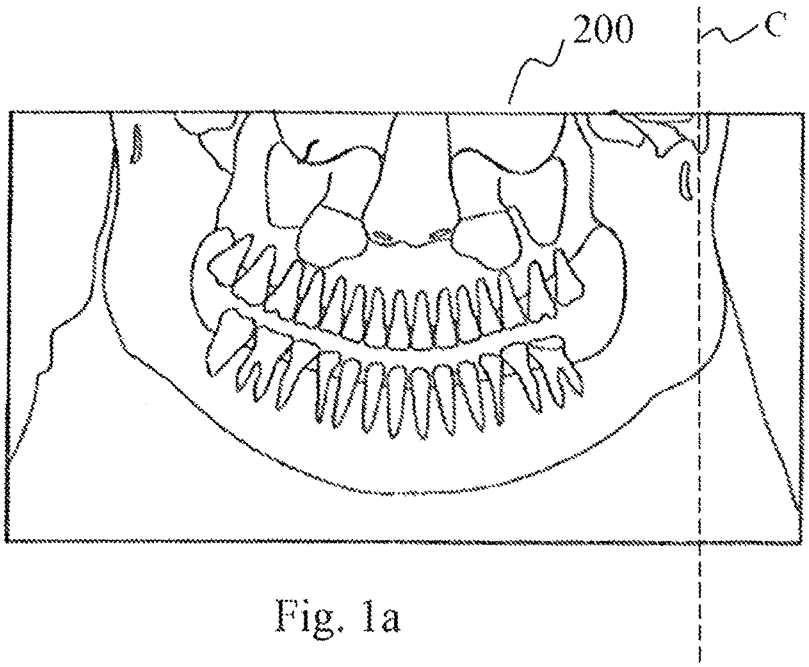
FIG. 1*a* shows a dental panoramic image and FIG. 1*b* an individual frame image, out of number of which a dental panoramic image may be generated.

A more complete understanding of the components, processes and apparatuses disclosed herein can be obtained by reference to the accompanying figures. The figures are merely schematic representations based on convenience and the ease of demonstrating features and are, therefore, not intended to indicate relative size and dimensions of devices or components thereof and/or to define or limit the scope of embodiments presented as examples.

Although specific terms may be used in the following description for the sake of clarity, such terms are intended to refer only to the particular structure of the embodiments selected for illustration in the drawings and are not intended to define or limit the scope of the disclosure.

The singular forms "a," "an," and "the" include plural referents unless the context clearly dictates otherwise.

As may be used herein, the terms about, generally and substantially are intended to encompass structural or numerical modifications which do not significantly affect the purpose of the element or number modified by such term.

As may be used in the specification and in the claims, the term "comprising" may include the embodiments "consisting of" and "consisting essentially of." The terms "comprise(s)," "include(s)," "having," "has," "can," "contain(s)," and variants thereof, when used herein, are intended to be open-ended transitional phrases, terms, or words that require the presence of the named elements/steps and permit the presence of other elements/steps.

Prior to going into more detailed discussion on the features of imaging and calibration according embodiments to this disclosure, while dental panoramic imaging is a preferable context in which these features may be applied, a brief overview of dental panoramic imaging is first presented for background.

The traditional operation principle of dental panoramic X-ray apparatuses includes driving an X-ray source and a film cassette around a patient's head while a film is moved with respect to the X-ray beam in such a way that the dental arch will get imaged as a planar picture on the film.

The basic operation of a traditional dental panoramic imaging system thus includes creating a respective mutual movement between the X-ray source, the image information receiver (film) and the patient. While there are number of possibilities to create such mutual movement, traditionally the most common arrangement has been to attach the X-ray source and the image information receiver to a support arm at a distance from each other, which arm is then moved in a specific way with respect to a stationary patient. In such context, in order to obtain a sharp image of a desired layer within the object, i.e. the layer of a dental arch inside a patient's head, the velocity of movement of the film has to be specifically correlated with the sweep velocity of the X-ray beam along the desired layer to be imaged. By this arrangement, the anatomies in front of and behind the desired layer within the patient's head are blurred invisible.

In such traditional dental panoramic imaging, the thickness of the layer that will be imaged sharp is directly proportional to the distance of the instantaneous center of rotation of the support arm from the film level, and inversely proportional to the magnification and to the width of the beam. This basic equation of panoramic imaging can be expressed as follows:

$$v1/v0 = L1/L0$$

$$v0 = \omega r$$

where:

L0=distance from the X-ray tube focus F to a point of the object being imaged at a given moment;

L1=distance from the X-ray tube focus F to the X-ray film (or detector) plane;

ω=angular velocity of rotational movement about the instantaneous center of rotation;

r=distance of the point of the object being imaged from the instantaneous center of rotation; and v1=velocity of the image point on the film (detector) plane.

The velocity v1 thus relates to the speed by which the film is moved during the panoramic imaging scan relative to the X-ray beam hitting the film.

As to digital imaging, when a so-called TDI imaging technique (Time Delayed Integration) is used, the transfer velocity of pixel charges across the detector is made to correspond to the velocity of film movement. Thus, the image data read out from a TDI detector will correspond to the panoramic film image in the sense that blurring of the layers outside the desired layer is already done when the scanning process and charge transfers are carried out so as to follow the above imaging equation. When using a frame detector and Frame Transfer (FT) technique, a number of individual overlapping frames are shot during the imaging scan and when one wishes to view the same layer as one would get when following the traditional panoramic imaging equation presented above, the degree of overlap of the frames when constructing the layer to be viewed as sharp shall be made to correspond to the velocity v1.

Figure 1B:
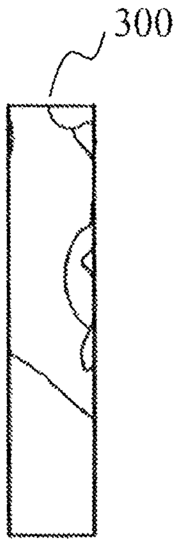
Figure 2:
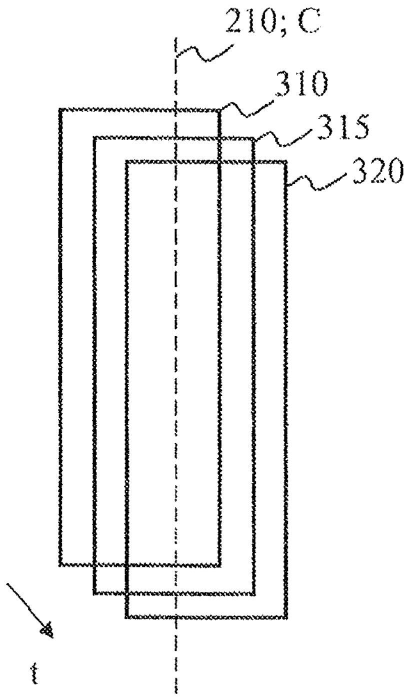
FIG. 2 shows individual overlapping frames together with a line representing a vertical section of an anatomy which is projected at different locations of the frames when an imaging detector is located at different exposure positions in relation to the anatomy.

FIG. 1A shows a typical dental panoramic image 200. When a digital panoramic image is constructed from frame image data acquired during a panoramic imaging scan, FIG. 1B can be considered representing one of hundreds or thousands of partially overlapping frame images 300 that are taken during the scan. FIG. 2 then shows a principle of how overlapping individual frames 310, 315, 320 acquired during a panoramic imaging scan can be used in constructing the digital panoramic image 200. Line 210 which vertically spans the frames 310, 315, 320 represents location of a pixel column in each of the frames which includes image information of the same thin vertical section of the anatomy being imaged. The image information these columns include is used to construct a pixel column C of the final digital panoramic image 200 to be generated, as to be discussed in more detail below. Frames taken before frame 310 and after frame 320 which do not intersect the line 210 and thus do not include information concerning the particular section of the anatomy line 210 represents, will not contribute to that particular column C of the panoramic image 200 being generated.

Figure 3:
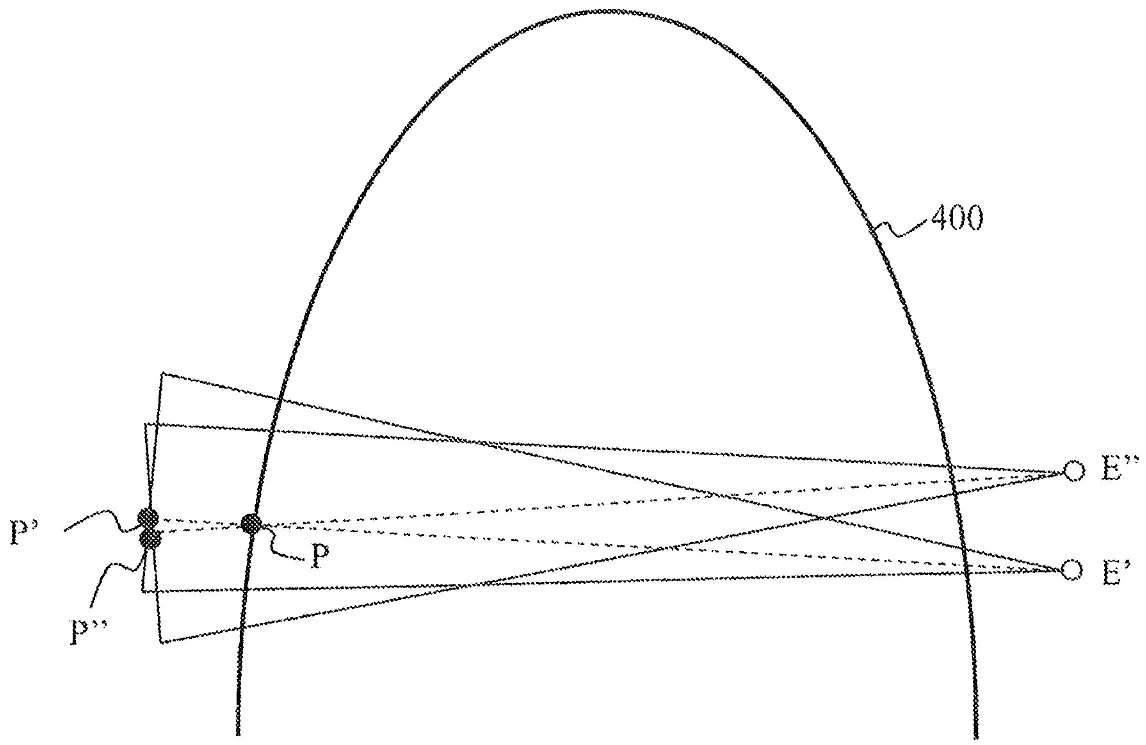
FIG. 3 is a schematic drawing of the principle of dental frame panoramic imaging process.

FIG. 3 shows a schematic drawing including what is called here a panoramic curve 400 as well as the imaging means in the coordinate system of this curve at two locations. In FIG. 3, point P represents location of a vertical layer of a dental arch which is to be shown as an individual pixel column in the final digital panoramic image being generated.

FIG. 3 further shows two exposure positions i.e. positions of the x-ray source (focus) E', E" and the detector at the time of an exposure and, thus, those of the X-ray beam which penetrates the anatomy being imaged and hitting the detector, as well as locations of corresponding projection points P', P" of point P. When such imaging geometry is known, one will be able to determine the location of projection P' of each point P on the detector, at each of the exposure positions in which a projection P' falls on the detector. These projection points P' determine pixel columns on the detector which are to be used in constructing the column C of the panoramic image.

Figure 4:
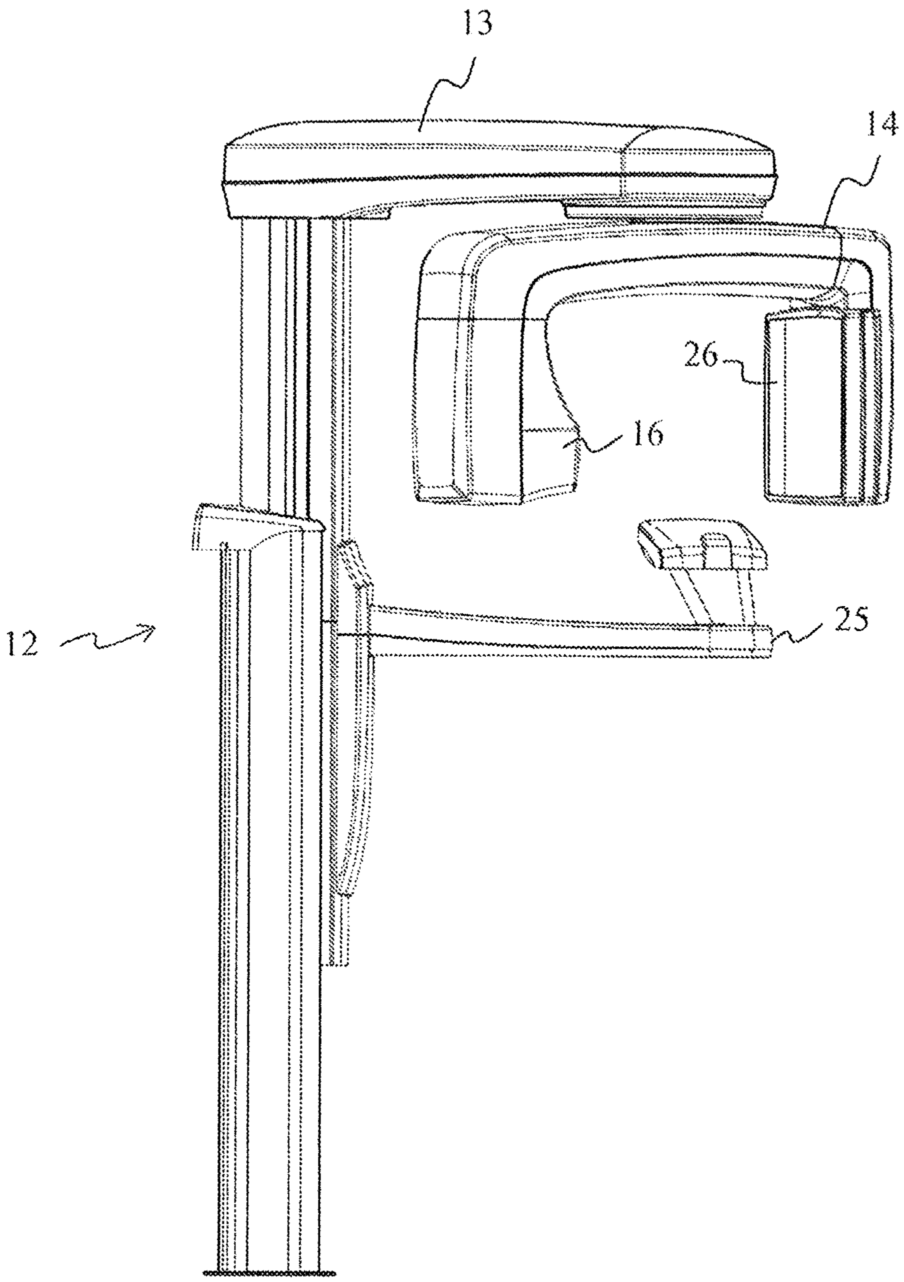
FIG. 4 shows an example of a dental panoramic imaging apparatus.

Presented in FIG. 4 is an example of an apparatus which can be used for dental panoramic radiography. The apparatus comprises a column-like vertically extending frame part 12 and a horizontally extending first supporting arm 13, which may be rotatably mounted on the upper end of the frame part 12. A second supporting arm 14, often referred to as a C-arm, is rotatably mounted at the outer end of the first supporting arm 13. The C-arm 14 supports the imaging means, i.e. an X-ray source 16 and an image detector 26. Moreover, a positioning support 25 is attached to the column-like frame part 12 to help in positioning the anatomy to be imaged. Instead of on the column-like frame part 12, the first supporting arm 13 may as well be mounted on wall or ceiling structures.

The second support arm 14 needs not to be, however, constructed as a C-arm as shown, and the apparatus may comprise structures not visible in the Fig. which enable further degrees of freedom of movement of e.g. the second supporting arm 14 in relation to the first supporting arm 13. The volume between the X-ray source and detector, which can be referred to as an imaging station space, does not necessarily include a positioning support 25 and, on the other hand, there may be such positioning support 25 which is configured to enable moving an anatomy supported by it within the imaging station space—such support may e.g. be a part of a chair arranged movable in relation to the imaging station space. Structures of dental panoramic imaging apparatus vary and at the simplest, the construction and control system may support just one fixed imaging geometry while perhaps typically, the apparatus are more versatile.

Figure 5:
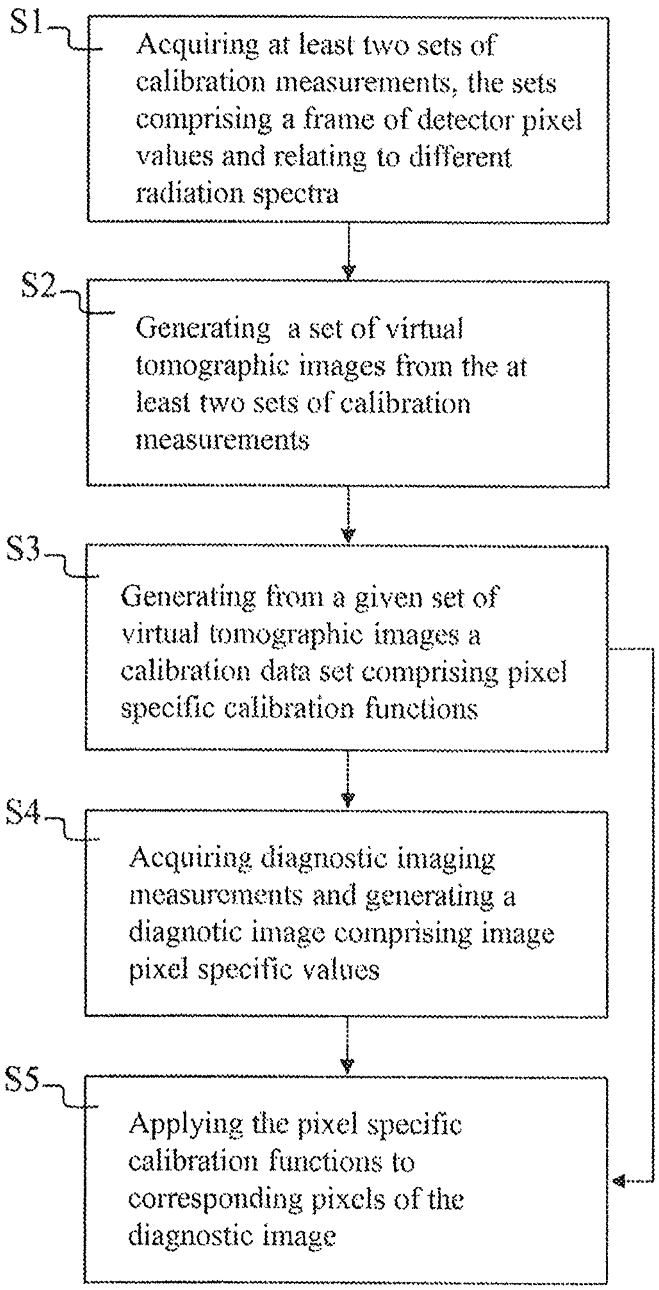
FIG. 5 shows steps of an imaging method implementing certain principles of a calibration method of this disclosure.

FIG. 5 illustrates some principles of an embodiment of method steps according to this disclosure. There, in step S1, at least two sets of calibration measurements using a tomographic imaging system are acquired, wherein an individual set of calibration measurements relates to a given radiation spectrum different from another given radiation spectrum, and wherein an individual set of calibration measurements comprises a frame of detector pixel values acquired during an exposure.

Acquiring the at least two sets of calibration measurements includes having an attenuator object of known attenuation characteristics in the X-ray beam during acquiring a given set of calibration measurements.

According to one embodiment, concerning using an attenuator object in the context of acquiring calibration measurements, preferably at least two objects of different known attenuation characteristics are used for acquiring calibration measurements of more than one attenuator object. A single calibration object may comprise two or more volumes of different materials. Acquiring calibration measurements of more than one attenuator object may comprise acquiring calibration measurements of any given attenuator object by a separate exposure.

As to the attenuator object, also the distance the X-ray beam will travel through the attenuator object during a calibration exposure is to be known. In the context of this disclosure, "the known dimensions" of the attenuator object refers to knowledge of distance the X-ray quanta (photons) need to travel through the attenuator object, i.e. it may not be necessary to have knowledge of all dimensions of the attenuator object.

In an embodiment, while the photons do not travel in parallel as they are generated at the focus of the X-ray source and diverge therefrom, one may take into account the variation in distances through the attenuator object there may be depending on location of a pixel in the detector.

Concerning attenuation characteristics including known dimensions of an attenuator object, in one preferable embodiment, more than one or two but like dozens of different sets of calibrations measurements are acquired using different calibration attenuator objects, which is prone to result in better quality of the final diagnostic images based on calibration as per this disclosure.

In step S2 of FIG. 5, regarding a given radiation spectrum and a related given individual set of calibration measurements, which can also be referred to as calibration data, a virtual tomographic image is generated by processing a frame of detector pixel values according to a diagnostic tomographic image frame processing procedure in which the calibration data is meant to be applied. That is, the single calibration data frame is considered to constitute a set of frames like there is or will be when imaging an anatomy. In other words, the single calibration data frame is multiplied, that is as many copies of it are made so as to get a set of identical frames of the same number as there is or will be frames when imaging an anatomy. Like in the context of dental panoramic imaging and referring to FIG. 2 discussed above, this can be considered like the single calibration data frame being duplicated so many times that one gets the same number of frames (frames like 310, 315, 320) as there has been or will be acquired when imaging an anatomy. While there are at least two sets of calibration measurements acquired in step S1, relating to different radiation spectra, at least two virtual tomographic images comprising virtual tomographic image pixel specific values are generated in step S2.

In step S3, then, from the thus generated at least two individual virtual tomographic images, a calibration tomographic image—which can be referred to as being a calibration tomographic image data set—is generated which comprises tomographic image pixel specific calibration functions. That is, at this stage of the method not detector pixels but tomographic image pixels are considered.

In step S4, which in embodiments may precede step S3, diagnostic tomographic imaging measurements of an anatomy are acquired, which measurements comprise several frames of detector pixel values, and these frames are processed according to the diagnostic tomographic imaging process in question—this processing including a corresponding processing as the one used when generating the virtual tomographic images. In step 5, then, the image pixel specific calibration functions generated in step S3 are applied to the corresponding pixels of the diagnostic tomographic image of the anatomy.

The pixel specific calibration functions are generated from the virtual tomographic image pixel data so as to model, for a given pixel, a spectral response of the imaging system based on the at least two radiation spectra used when acquiring the calibration measurements. In an embodiment, a mathematical function is used which describes the pixel response to changing of the X-ray spectrum. This response is typically different for two or more spectral measurements. The changing spectrum may represent attenuator objects in the beam versus flat field, for example. The principal purpose of the calibration is to fit the functions so that they best correspond experimental measurements.

The calibration functions may also be different depending on the purpose they are designed to be applied for. This may include e.g. taking into account so called beam hardening of radiation when penetrating an object or applying the calibration functions in generating material decomposed images, like shown in FIG. 6 (from the native image, soft and a hard tissue images are generated). No specific kind calibration function needs to be generated as a consequence of the calibration data being what is termed here "a virtual tomographic image", as compared to any other kind frame-based calibration images. As to how to generate such functions in more detail, reference can be made to e.g. an article Coleman A. J. and Sinclair M., A beam-hardening correction using dual-energy computed tomography, Phys Med Biol, 1985 November; 30(1-1):1251-1256, as well as articles Schlomka J. P. et al., Experimental feasibility of multi-energy photon-counting K-edge imaging in pre-clinical computed tomography and Mechlem K. et al., Spectral angiography material decomposition using an empirical forward model and a dictionary-based regularization, IEEE Transactions on Medical Imaging, 2018; 37(10):2298-2309, which all are incorporated herein by reference.

According to one aspect, as an example, a calibration function for two materials and two spectral measurements may comprise using low-order polymonials to model log-signals $$l_i^s$$

as a function material thicknesses $$A_i^n.$$

Here, the expected number of counts for pixel i and spectral measurement s is defined as:

$$\hat{y}_i^s = b_i^s e^{-\hat{l}_i^s},\ \hat{l}_i^s = P_i^s(A_i; C_{is}),\ A_i = \left(A_i^0, \ldots , A_i^n\right)^T$$

where $$b_i^s$$

is the flatfield signal for pixel i and spectral measurements. The polynomial model $$P_i^s$$

in this case consists of two basis materials:

$$P_i^s = \frac{N}{D}$$

$$N = c_0 + c_1 A_i^0 + c_2 A_i^1 + c_3\left(A_i^0\right)^2 + c_4\left(A_i^1\right)^2 + c_5 A_i^0 A_i^1$$

$$D = 1 + c_6 A_i^0 + c_7 A_i^1$$

where c are the fit coefficients.

A least-squares fit to the calibration measurements is carried out to find the fit parameters cis:

$$c_{is} = \operatorname{argmin} \sum_{k=1}^{K} W_k (l_{ik}^s - P(A_{ik}; c_{is}))^2$$

where $$l_{ik}^s$$

are linearized calibration measurements, $$A_{ik}^k$$

are the material thicknesses, and $w_k$ the weights with k being the calibration measurement index.

Regarding step S2 discussed above, when a given set of calibration measurements acquired in step S1 is one single frame of detector pixel values, in embodiments of this disclosure, generating the virtual tomographic image includes, as already discussed, taking that single frame to represent a set of frames as acquired during diagnostic imaging of an anatomy, wherein all those frames of such set then just have identical detector pixel values. That is, in case the diagnostic imaging in the context of which the virtual tomographic image is to be used as base calibration data includes e.g. processing detector pixel values of a number of frames by summing pixel values of the frames as partially overlapping each other, pixel values of that single calibration data frame are summed with other values of that single frame according to that particular partial overlapping procedure of that given particular diagnostic imaging process.

The idea of the above steps may thus be presented being that, instead of using a native frame or any number of native frames of calibration measurements as such and then generate detector pixel specific calibration functions, virtual tomographic images are first generated from the calibration measurements and based on those, image pixel specific calibration functions. These calibration functions based on such virtual tomographic images are then applied to image data generated from diagnostic imaging results of an anatomy. That is, one does not "compare" data of native calibration frames and native diagnostic imaging frames but virtual tomographic images are first generated from the native calibration frames, and a diagnostic tomographic image from the native diagnostic imaging frames, and wherein both kinds of tomographic images are generated from the native detector frames using the same detector frame data processing method.

While a term virtual tomographic image has been used above, an alternative to be used could be virtual tomographic calibration image, or virtual tomographic calibration data.

According to one embodiment, the at least two different radiation spectra used when acquiring the at least two calibration measurements are different spectra generated by an X-ray source.

According to one embodiment, the at least two different radiation spectra used when acquiring the at least two calibration measurements are spectra filtered differently upon being generated by the X-ray source.

According to one embodiment, the detector used in the imaging system is a detector configured to provide at least two different pixel data sets based on a given single radiation exposure.

According to one embodiment, a photon counting detector with at least two bins configured to count photons of different energy ranges is used.

According to one embodiment, a method can be used in which in the first step S1, calibration measurements are acquired, where "calibration measurements" refers to a set of pixel counts of a frame of a photon counting detector, detected upon a calibration exposure, and wherein individual detector pixels comprise at least two bins so that there are at least two counts from an individual pixel covering at least two energy ranges the detector is configured to detect. That is, in case of a pixel with two bins there may be one with a lower and one with a higher photon energy detecting threshold.

When acquiring an individual set of calibration measurements, according to one embodiment, again, an attenuator object of known material (known in the sense of how it attenuates radiation) with known dimension(s) is placed within the path of the X-ray beam from the X-ray source to the image detector. Such object or more than one such object may comprise sections of more than one known material and dimensions while, preferably and as discussed, attenuators of at least two different known attenuating characteristics are used to acquire at least two sets of calibration measurements based on two different materials.

When acquiring the calibration measurements, as also in the context of the example according to FIG. 5, preferably the same or close to the same exposure parameter values are used as will be used upon an actual diagnostic imaging of an anatomy—possibly apart from that one may consider using upon acquiring calibration results a longer exposure time to ensure a reasonable number of hits of photons at the detector pixels.

According to such embodiment in the second step S2, then, based on a given set of calibration measurements, a virtual panoramic image may be generated by summing pixel counts of the frame columns of an individual calibration measurement set, i.e. an individual calibration exposure frame, the same way as will be done or has been done according to the imaging process that is used upon a given diagnostic dental panoramic imaging. While in the context of an example of using such photon counting detector as discussed above there are at least two counts per pixel, one may consider a virtual panoramic image thus generated comprising, for any given image pixel, the same number of pixel values as is the number of energy ranges (pixel bins) used when acquiring the calibration measurements—or consider that there is such number virtual panoramic images generated relating to a given calibration exposure.

So, according to one embodiment, as an example and like discussed when referring to FIG. 5, acquiring calibration measurements may comprise a stationary exposure i.e. one in which none of the X-ray source, detector and attenuator object moves during acquisition, and generating the virtual tomographic image from that single calibration frame then includes summing of the pixel counts of the frame the same way as if there would be the same number of frames that are acquired according to the dental panoramic diagnostic imaging process. Again, reference can be made here to FIG. 3 and the related description above.

In view of quality of the diagnostic images to be generated while applying the calibration measurements, as discussed, it is preferable to acquire a sufficient number of sets of calibration measurements and to generate based on them a sufficient number of corresponding virtual dental panoramic images. That is, based on having used different attenuator objects and/or sets of attenuator objects, like 15 or even much more. It is, thus, preferable to repeat a sequence of steps S1-S2 several times by using different attenuator objects or attenuator object sets. Further and as also already noted, sufficiently long exposure times may be preferable to be used in step S1, in order to get when using a photon counting detector a reasonable number of photon counts at the detector pixel bins for any given attenuator object or attenuator object set.

In the third step S3 of such embodiment, then, when now having a set of virtual panoramic images generated as discussed above, pixel specific calibration functions to be applied on diagnostic panoramic image data may be determined.

Upon the actual diagnostic imaging of an anatomy (S4), panoramic imaging measurements (counts) of an anatomy are acquired regarding two or more photon energy ranges, to be used in generating panoramic images of the anatomy. The pixel specific calibration functions are then applied to the corresponding panoramic image pixel specific counts of the panoramic images (S5).

In the context of dental panoramic imaging according to this example, the calibration functions may be configured to generate two panoramic images out of which a first represents hard tissue and another soft tissue. As an example of how to realize that, a reference can be made to e.g. the Roessl and Proksa, and Melchem et al. articles mentioned above.

Figure 6:
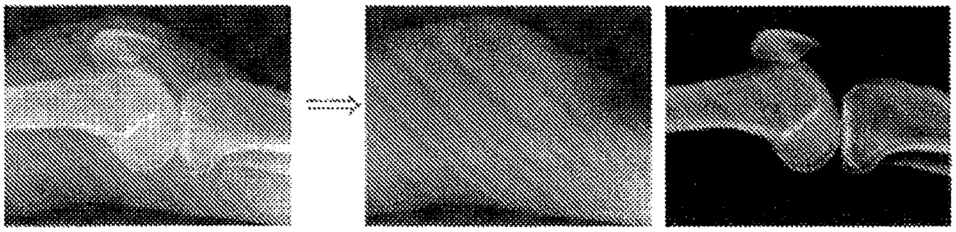
FIG. 6 shows an example of decomposition of an X-ray image into a bone tissue and a soft tissue image.

Again, FIG. 6 is an example showing material decomposition of a traditional X-ray image into a hard tissue image and a soft tissue image.

In embodiments of this disclosure, the detector may comprise also another kind of construction than the at least two bin photon counting pixel to enable at least two values based on different detecting criteria to be detected so as to provide for a given exposure at least two sets of detector pixel values.

Figure 7:
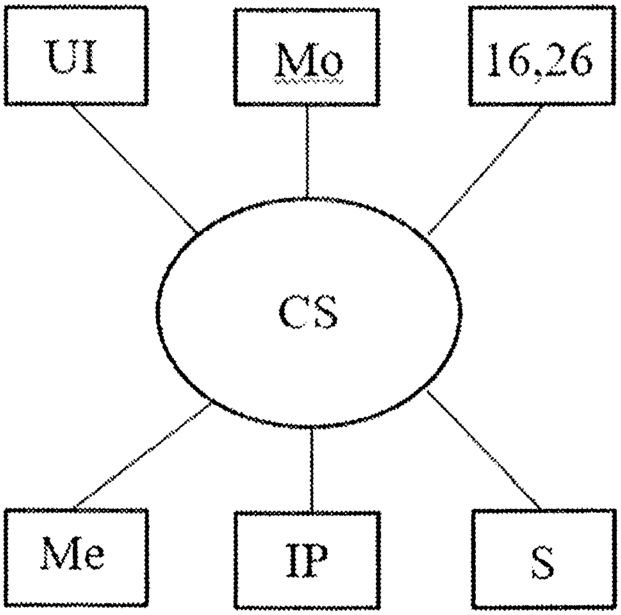
FIG. 7 shows some components of a system, as an example, by which embodiments of this disclosure can be realized.

Some components of a system using which one may be able to implement embodiments of this disclosure may include, as shown in FIG. 7, a control system CS of the imaging apparatus, which includes or is in operational connection with motors (Mo) that drive e.g. one or more arms or other structures of the imaging apparatus, with operating electronics relating to controlling the X-ray source (16) and image detector (26). The system may further include a memory (Me) for, as an example, recording frame image information and information regarding imaging geometry, processing means (IP) to create a panoramic or other tomographic image and to optionally perform other data processing, a screen (S) on which to show images and a user interface (UI).

Figure 8:
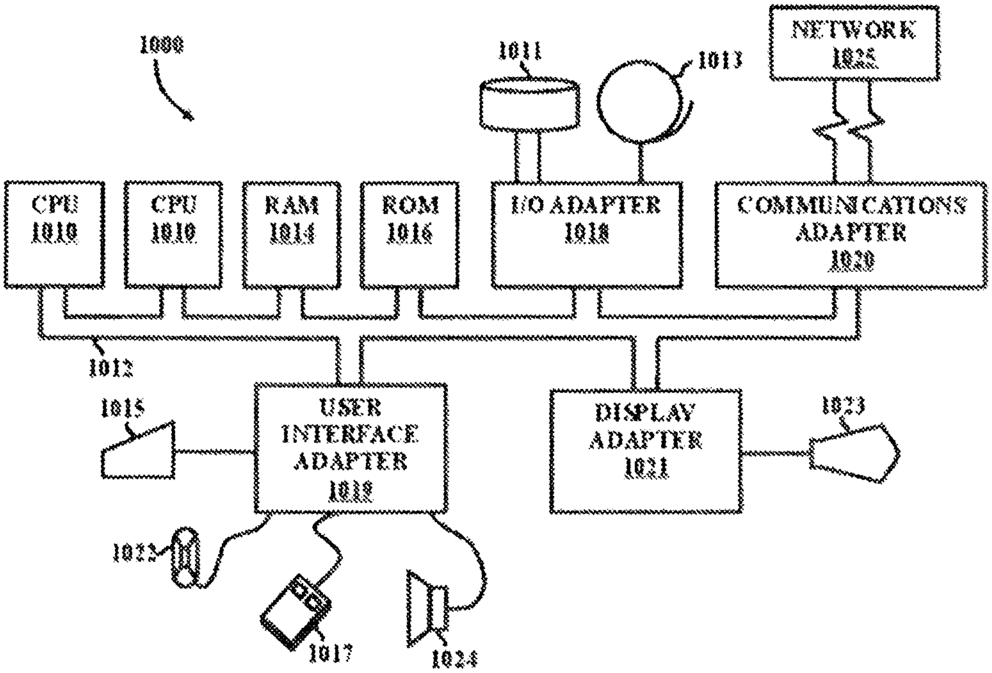
FIG. 8 shows a schematic drawing illustrating a hardware configuration, as an example, of an information handling/computer system which can be used when implementing embodiments of this disclosure.

FIG. 8 is a schematic drawing which illustrates a hardware configuration of an information handling/computer system. System 1000 of FIG. 8 comprises at least one processor or central processing unit (CPU) 1010. The CPUs 1010 are interconnected via system bus 1012 to various devices such as a random-access memory (RAM) 1014, read-only memory (ROM) 1016, and an input/output (I/O) adapter 1018. The I/O adapter 1018 can connect to peripheral devices, such as disk units 1011 and tape drives 1013, or other program storage devices that are readable by system 1000. System 1000 can read the inventive instructions on the program storage devices and follow these instructions to execute the methodology of the embodiments herein. The system further includes a user interface adapter 1019 that connects a keyboard 1015, mouse 1017, speaker 1024, microphone 1022, and/or other user interface devices such as a touch screen device (not shown) to the bus 1012 to gather user input. Additionally, a communication adapter 1020 connects the bus 1012 to a data processing network 1025, and a display adapter 1021 connects the bus 1012 to a display device 1023 which may be embodied as an output device such as a monitor, printer, or transmitter, for example.

Concerning the discussion above relating dental panoramic imaging, in case having an imaging system which allows for using more than one imaging geometry, when having stored in a memory the native calibration measurements, it is possible to generate virtual panoramic images and thus image pixel specific calibration functions corresponding to any such geometry and then store those, to be practically readily available for use when needed.

While some of the discussion above refers specifically to dental panoramic imaging, photon counting detectors and material decomposition, some of the details discussed are not specific to such context but may be applied, just as to give some examples, in the context of also other tomographic imaging like in tomosynthesis. Also, other than photon counting detectors may be used, also regarding getting two or more pixel specific values from a single exposure. One example where to apply embodiments discussed above is tomosynthesis used in the context of mammography, regarding which one often talks about digital breast tomosynthesis (DBT).

To summarize and present the above disclosure partially in other words, this disclosure teaches a tomographic imaging method wherein an imaging system is used which comprises an X-ray source generating a radiation spectrum and a detector comprising a two-dimensional frame of detector pixels, the imaging method comprising:

- using the imaging system to acquire calibration data;
- using the imaging system to acquire a set of frame image data of an anatomy, which acquiring comprises using the X-ray source to expose the anatomy from different directions and detecting by the detector radiation penetrating the anatomy from said different directions, the mutual positions of the X-ray source;
- generating at least one tomographic image of the anatomy comprising tomographic image pixel specific values by applying a frame image data processing method to said set of frame image data of the anatomy.

Upon generating the at least one tomographic image of the anatomy tomographic image pixel specific calibration functions are applied on the tomographic image pixel specific values, the tomographic image pixel specific calibration functions being generated based on virtual tomographic images, wherein a given single virtual tomographic image is generated based on a single detector pixel frame data acquired upon a single calibration exposure of an attenuator object, which generating the virtual tomographic image comprises considering, in pracise multiplying the detector pixel frame data acquired upon the calibration exposure of the attenuator object to constitute a set of calibration data frames having the same number of frames as there are in said set of frame image data of the anatomy, and applying to such set of calibration data frames the same frame image data processing method as applied to said set of frame image data of the anatomy.

In an embodiment, then, prior to or after acquiring the set of frame image data of the anatomy, calibration data is acquired relating to at least two different radiation spectra, which acquiring concerning a given of said at least two radiation spectra comprises acquiring said calibration data by using the X-ray source to expose an attenuator object of known radiation attenuation characteristics and detecting by the detector radiation penetrating the attenuator object, whereby an attenuator data frame comprising detector pixel specific values is acquired, wherein concerning acquiring a given single attenuator data frame of detector pixel specific values, the distance the radiation travels through the attenuator object when acquiring the detector pixel specific values of said attenuator data frame is known and, concerning a given radiation spectrum of the at least two radiation spectra, a virtual tomographic calibration image is generated from the calibration data, wherein generating the virtual tomographic calibration image comprises considering, in practice multiplying said given single attenuator data frame of detector pixel specific values to constitute such set of attenuator data frames which as for the number of frames corresponds to the set of frame image data of the anatomy acquired when acquiring the set of frame image data of the anatomy and used in generating the tomographic image of the anatomy, and wherein the same frame data processing method is applied to such set of attenuator data frames as the one applied to the set of frame image data acquired or to be acquired when acquiring the set of frame image data of the anatomy. Tomographic image pixel specific calibration functions are generated from the thus generated at least two virtual tomographic calibration images relating to the at least two different radiation spectra, while the detector is a detector configured to provide, regarding an individual detector pixel, at least two values based on different detecting criteria so as to provide for a given exposure at least two sets of detector pixel values, whereby acquiring the set of frame image data of the anatomy comprises acquiring at least two sets of frame image data of the anatomy based on said different detecting criteria, and wherein generating said tomographic image of the anatomy comprising image pixel specific values comprises generating at least two tomographic images of the anatomy based on said detected at least two sets of frame image data of the anatomy, and wherein the tomographic image pixel specific calibration functions are applied to the corresponding image pixel specific values of the at least two tomographic images of the anatomy.

In an embodiment, the X-ray source and the detector are components of a mammography imaging system and the frame data processing method applied to the attenuator data frame or frames to generate the virtual tomographic calibration image or images, and applied to the set or sets of frame image data of the anatomy, comprises steps of a digital breast tomosynthesis method.

In an embodiment, the frame data processing method applied to the attenuator data frame or frames to generate the virtual tomographic calibration image or images, and applied to the set or sets of frame image data of the anatomy, comprises steps of summing frames of a given set of detector frame pixel specific values as the frames partially overlapping each other.

In an embodiment, the X-ray source and the detector are components of a dental panoramic imaging system and the frame data processing method applied to the attenuator data frames to generate the virtual tomographic calibration image or images, and applied to the set or sets of frame image data of the anatomy, comprises steps of summing frames of a given set of detector frame pixel specific values as the frames partially overlapping each other according a dental panoramic imaging process the dental imaging system is configured to apply.

In an embodiment, the acquiring of the calibration data includes using attenuator objects of different attenuation characteristics and/or different dimensions.

In an embodiment, the at least two radiation spectra used when acquiring calibration data include different spectra generated by the X-ray source or spectra filtered differently upon being generated by the X-ray source.

In an embodiment, the tomographic image pixel specific calibration functions are configured to, when applied to the at least two tomographic images of the anatomy, generate material decomposed tomographic images.

In an embodiment, the tomographic image pixel specific calibration functions are configured to, when applied to the at least two tomographic images of an anatomy, compensate for X-ray beam hardening when penetrating an object.

In an embodiment, the detector is a photon counting detector comprising pixels with at least two bins configured to detect photons of different energy ranges, and to thereby provide for a given exposure at least two sets of detector pixel values.

This disclosure further teaches a method for generating calibration data for dental panoramic imaging, wherein a dental panoramic imaging system is used to acquire frame image data, the dental panoramic imaging system comprising an X-ray source generating a radiation spectrum and a detector comprising a two-dimensional frame of detector pixels, wherein generating the calibration data comprises generating panoramic image pixel specific calibration functions to be applied to panoramic image pixel specific values acquired when imaging an anatomy, the panoramic image pixel specific calibration functions being generated based on virtual panoramic images, wherein a given single virtual panoramic image is generated based on detector pixel frame data acquired upon a single calibration exposure of an attenuator object, which generating the virtual panoramic image comprises considering, in practice multiplying the detector pixel frame data acquired upon the single calibration exposure of the attenuator object to constitute a set of calibration data frames having the same number of frames as there are in a set of frame image data acquired when imaging an anatomy, and applying to such set of calibration data frames the same frame image data processing method as applied to said set of frame image data of the anatomy when generating a panoramic image of an anatomy.

In an embodiment, then, calibration data is acquired relating to at least two different radiation spectra, which acquiring concerning a given of said at least two radiation spectra comprises acquiring said calibration data by using the X-ray source to expose an attenuator object of known radiation attenuation characteristics and detecting by the detector radiation penetrating the attenuator object whereby an attenuator data frame of detector pixel specific values is acquired, wherein concerning acquiring a given single attenuator data frame of detector pixel specific values, the distance the radiation travels through the attenuator object when acquiring the detector pixel specific values of said attenuator data frame is known, and wherein concerning a given radiation spectrum of the at least two radiation spectra, a virtual panoramic calibration image is generated from the calibration data, wherein generating the virtual panoramic calibration image comprises considering, in practice multiplying said given single attenuator data frame of detector pixel specific values to constitute such set of attenuator data frames which as for the number of frames corresponds to a set of image data frames of an anatomy acquired when acquiring a set of frame image data of an anatomy and used in generating a dental panoramic image of the anatomy, and wherein a frame data processing method is applied to such set of attenuator data frames which is the same as one applied to a set of image data frames of an anatomy acquired when acquiring a set of frame image data of an anatomy, wherein the frame data processing method comprises steps of summing frames of a given set of detector frame pixel specific values as the frames partially overlapping each other, and wherein panoramic image pixel specific calibration functions are generated from the thus generated at least two virtual panoramic calibration images relating to the at least two different radiation spectra, the panoramic image pixel specific calibration functions being configured to be applied to values of corresponding image pixels of a panoramic image of an anatomy.

In an embodiment, acquiring of calibration data includes using attenuator objects of different attenuation characteristics and/or different dimensions.

In an embodiment, the at least two radiation spectra used when acquiring calibration data are different spectra generated by the X-ray source or spectra filtered differently upon being generated by the X-ray source.

In an embodiment, the detector is a detector configured to provide, regarding an individual detector pixel, at least two values based on different detecting criteria so as to provide for a given exposure at least two sets of detector pixel values, and the panoramic image pixel specific calibration functions are configured to be applied to pixel values of pixels of at least two panoramic images of an anatomy generated based on such at least two sets of detector pixel values.

In an embodiment, the panoramic image pixel specific calibration functions are configured to, when applied to the at least two panoramic images of an anatomy, generate material decomposed panoramic images.

In an embodiment, the panoramic image pixel specific calibration functions are configured to, when applied to the at least two panoramic images of an anatomy, compensate for X-ray beam hardening when penetrating an object.

In an embodiment, the detector is a photon counting detector comprising pixels with at least two bins configured to detect photons of different energy ranges, and thereby to provide for a given exposure at least two sets of detector pixel values.

This disclosure further teaches a dental panoramic imaging system, comprising:

- an X-ray source generating a radiation spectrum and a detector comprising a two-dimensional frame of detector pixels;
- a first support construction configured to support the X-ray source and the detector, wherein the first support construction is configured to support the X-ray source and the detector at a distance from each other so as to define between them an imaging station space, and optionally a second support construction designed to support an anatomy and arranged to extend within the imaging station space;
- at least either of i) a driving construction configured to move the X-ray source and the detector in relation to the imaging station space and ii) a driving construction configured move the second support construction;

a data processing device, and a data communication link configured to enable the data processing device receive information from the detector, wherein the dental panoramic imaging system optionally comprises a dental panoramic imaging apparatus comprising the X-ray source and the detector and the data processing device arranged as integrated with the apparatus;

a control system, and wherein the control system comprises a first operation mode and a second operation mode and is configured to, in the first operation mode, during an imaging exposure and while information is being detected at the detector, cause at least one of said i) X-ray source and detector and ii) the second support construction to move so that there will be both mutual rotational and linear movement in relation to the imaging station space, and wherein the control system is configured for both i) acquiring in the first operation mode a set of frame image data of an anatomy, which acquiring comprises using the X-ray source to expose the anatomy locating within the imaging station space from different directions and detecting by the detector radiation penetrating the anatomy from said different directions, and ii) acquiring in the second operation mode during a calibration exposure calibration data comprising detector pixel specific values, and wherein the data processing device is configured to generate a dental panoramic image comprising image pixel specific values by applying a frame data processing method to said set of frame image data of an anatomy, and wherein the data processing device is configured in the second operation mode to receive calibration data relating to at least two different radiation spectra, wherein the calibration data concerning a given of said at least two radiation spectra has been acquired by using the X-ray source to expose an attenuator object of known radiation attenuation characteristics and detecting by the detector radiation penetrating the attenuator object, whereby an attenuator data frame of detector pixel specific values is acquired, wherein concerning acquiring a given single attenuator data frame of detector pixel specific values, the distance the radiation travels through the attenuator object when acquiring the detector pixel specific values of said attenuator data frame is known, and wherein concerning a given radiation spectrum of the at least two radiation spectra, the data processing device is configured to generate a virtual panoramic calibration image from the calibration data, wherein generating the virtual panoramic calibration image comprises considering, in practice multiplying said given single attenuator data frame of detector pixel specific values to constitute such set of attenuator data frames which as for the number of frames corresponds to the set of frame image data of the anatomy acquired when acquiring the set of frame image data of the anatomy and used in generating the panoramic image of the anatomy, wherein the same frame data processing method is applied to such set of attenuator data frames as the one applied to the set of frame image data acquired or to be acquired when acquiring the set of frame image data of the anatomy, and to generate panoramic image pixel specific calibration functions from the thus generated at least two virtual panoramic calibration images relating to the at least two different radiation spectra.

In an embodiment, the detector is a detector configured to provide, regarding an individual detector pixel, at least two values based on different detecting criteria so as to provide for a given exposure at least two sets of detector pixel values, and wherein the data processing device is configured to receive at least two sets of frame image data of an anatomy based on said different detecting criteria and to generate said panoramic image of the anatomy comprising image pixel specific values, wherein said generating comprises generating at least two panoramic images of the anatomy based on said detected at least two sets of frame image data of the anatomy, and to apply the panoramic image pixel specific calibration functions to the corresponding image pixel specific values of the at least two panoramic images of the anatomy.

In an embodiment, the detector is a photon counting detector comprising pixels with at least two bins configured to detect photons of different energy ranges, and thereby to provide for a given exposure at least two sets of detector pixel values.

In an embodiment, the panoramic image pixel specific calibration functions are configured to, when applied to the at least two panoramic images of an anatomy, generate material decomposed panoramic images.

In an embodiment, the detector is a photon counting detector comprising pixels with at least two bins, the bins being configured to count photons of different energy ranges, and the data processing device is configured to use, as said at least two sets of detector frame pixel specific values, sets of detector frame pixel specific values counted by the at least two bins during an exposure.

The invention claimed is:

1. Tomographic imaging method, wherein an imaging system is used which comprises an X-ray source generating a radiation spectrum and a detector comprising a two-dimensional frame of detector pixels, the imaging method comprising:

using the imaging system to acquire calibration data;

using the imaging system to acquire a set of frame image data of an anatomy, which acquiring comprises using the X-ray source to expose the anatomy from different directions and detecting by the detector radiation penetrating the anatomy from said different directions;

generating at least one tomographic image of the anatomy comprising tomographic image pixel specific values by applying a frame image data processing method to said set of frame image data of the anatomy, characterized in that upon generating the at least one tomographic image of the anatomy, tomographic image pixel specific calibration functions are applied on the tomographic image pixel specific values, the tomographic image pixel specific calibration functions being generated based on virtual tomographic images, wherein a given single virtual tomographic image is generated based on a single detector pixel frame data acquired upon a single calibration exposure of an attenuator object, which generating the virtual tomographic image comprises multiplying the single detector pixel frame data acquired upon the calibration exposure of the attenuator object to constitute a set of calibration data frames having the same number of frames as there are in said set of frame image data of the anatomy, and applying to such set of calibration data frames the same frame image data processing method as applied to said set of frame image data of the anatomy.

2. Tomographic imaging method according to claim 1, characterized in that prior to or after acquiring the set of frame image data of the anatomy, calibration data is acquired relating to at least two different radiation spectra, which acquiring concerning a given of said at least two radiation spectra comprises acquiring said calibration data by using the X-ray source to expose an attenuator object of known radiation attenuation characteristics and detecting by the detector radiation penetrating the attenuator object of known radiation attenuation characteristics, whereby an attenuator data frame comprising detector pixel specific values is acquired, wherein concerning acquiring a given single attenuator data frame of detector pixel specific values, a distance the radiation travels through the attenuator object of known radiation attenuation characteristics when acquiring the detector pixel specific values of said attenuator data frame is known;

concerning a given radiation spectrum of the at least two radiation spectra, a virtual tomographic calibration image is generated from the calibration data, wherein generating the virtual tomographic calibration image comprises multiplying said given single attenuator data frame of detector pixel specific values to constitute such set of attenuator data frames which as for the number of frames corresponds to the set of frame image data of the anatomy acquired when acquiring the set of frame image data of the anatomy and used in generating the tomographic image of the anatomy, and wherein the same frame data processing method is applied to such set of attenuator data frames as the one applied to the set of frame image data acquired or to be acquired when acquiring the set of frame image data of the anatomy;

tomographic image pixel specific calibration functions are generated from the thus generated at least two virtual tomographic calibration images relating to the at least two different radiation spectra, and wherein the detector is a detector configured to provide, regarding an individual detector pixel, at least two values based on different detecting criteria so as to provide for a given exposure at least two sets of detector pixel values, whereby acquiring the set of frame image data of the anatomy comprises acquiring at least two sets of frame image data of the anatomy based on said different detecting criteria, and wherein generating said tomographic image of the anatomy comprising image pixel specific values comprises generating at least two tomographic images of the anatomy based on said detected at least two sets of frame image data of the anatomy, and wherein the tomographic image pixel specific calibration functions are applied to the corresponding image pixel specific values of the at least two tomographic images of the anatomy.

3. Tomographic imaging method according to claim 2, characterized in that the X-ray source and the detector are components of a mammography imaging system and the frame data processing method applied to the attenuator data frame or frames to generate the virtual tomographic calibration image or images, and applied to the set or sets of frame image data of the anatomy, comprises steps of a digital breast tomosynthesis method.

4. Tomographic imaging method according to claim 2, characterized in that the frame data processing method applied to the attenuator data frame or frames to generate the virtual tomographic calibration image or images, and applied to the set or sets of frame image data of the anatomy, comprises steps of summing frames of a given set of detector frame pixel specific values as the frames partially overlapping each other.

5. Tomographic imaging method according to claim 4, characterized in that the X-ray source and the detector are components of a dental panoramic imaging system and the frame data processing method applied to the attenuator data frames to generate the virtual tomographic calibration image or images, and applied to the set or sets of frame image data of the anatomy, comprises steps of summing frames of a given set of detector frame pixel specific values as the frames partially overlapping each other according a dental panoramic imaging process the dental panoramic imaging system is configured to apply.

6. Tomographic imaging method according to claim 2, characterized in that the at least two radiation spectra used when acquiring calibration data include different spectra generated by the X-ray source or spectra filtered differently upon being generated by the X-ray source.

7. Tomographic imaging method according to claim 1, characterized in that the acquiring of the calibration data includes using attenuator objects of different attenuation characteristics and/or different dimensions.

8. Tomographic imaging method according to claim 1, characterized in that the tomographic image pixel specific calibration functions are configured to, when applied to the at least two tomographic images of the anatomy, generate material decomposed tomographic images.

9. Tomographic imaging method according to claim 1, characterized in that the tomographic image pixel specific calibration functions are configured to, when applied to the at least two tomographic images of an anatomy, compensate for X-ray beam hardening when penetrating an object.

10. Tomographic imaging method according to claim 1, characterized in that the detector is a photon counting detector comprising pixels with at least two bins configured to detect photons of different energy ranges, and to thereby provide for a given exposure at least two sets of detector pixel values.

11. Method for generating calibration data for dental panoramic imaging, wherein a dental panoramic imaging system is used to acquire frame image data, the dental panoramic imaging system comprising an X-ray source generating a radiation spectrum and a detector comprising a two-dimensional frame of detector pixels, characterized in that generating the calibration data comprises generating panoramic image pixel specific calibration functions to be applied to panoramic image pixel specific values acquired when imaging an anatomy, the panoramic image pixel specific calibration functions being generated based on virtual panoramic images, wherein a given single virtual panoramic image is generated based on detector pixel frame data acquired upon a single calibration exposure of an attenuator object, which generating the virtual panoramic image comprises multiplying the detector pixel frame data acquired upon the single calibration exposure of the attenuator object to constitute a set of calibration data frames having the same number of frames as there are in a set of frame image data acquired when imaging the anatomy, and applying to such set of calibration data frames the same frame image data processing method as applied to said set of frame image data of the anatomy when generating a panoramic image of the anatomy.

12. Method according to claim 11, characterized in that calibration data is acquired relating to at least two different radiation spectra, which acquiring concerning a given of said at least two radiation spectra comprises acquiring said calibration data by using the X-ray source to expose an attenuator object of known radiation attenuation characteristics and detecting by the detector radiation penetrating the attenuator object of known radiation attenuation characteristics whereby an attenuator data frame of detector pixel specific values is acquired, wherein concerning acquiring a given single attenuator data frame of detector pixel specific values, the distance the radiation travels through the attenuator object of known radiation attenuation characteristics when acquiring the detector pixel specific values of said attenuator data frame is known, wherein concerning a given radiation spectrum of the at least two radiation spectra, a virtual panoramic calibration image is generated from the calibration data, wherein generating the virtual panoramic calibration image comprises multiplying said given single attenuator data frame of detector pixel specific values to constitute such set of attenuator data frames which as for the number of frames corresponds to a set of image data frames of the anatomy acquired when acquiring a set of frame image data of the anatomy and used in generating a dental panoramic image of the anatomy, and wherein a frame data processing method is applied to such set of attenuator data frames which is the same as one applied to a set of image data frames of the anatomy acquired when acquiring a set of frame image data of an anatomy, wherein the frame data processing method comprises steps of summing frames of a given set of detector frame pixel specific values as the frames partially overlapping each other, and wherein panoramic image pixel specific calibration functions are generated from the thus generated at least two virtual panoramic calibration images relating to the at least two different radiation spectra, the panoramic image pixel specific calibration functions being configured to be applied to values of corresponding image pixels of a panoramic image of the anatomy.

13. Method according to claim 12, characterized in that the acquiring of calibration data includes using attenuator objects of different attenuation characteristics and/or different dimensions.

14. Method according to claim 12, characterized in that the at least two radiation spectra used when acquiring calibration data are different spectra generated by the X-ray source or spectra filtered differently upon being generated by the X-ray source.

15. Method according to claim 12, characterized in that the detector is a detector configured to provide, regarding an individual detector pixel, at least two values based on different detecting criteria so as to provide for a given exposure at least two sets of detector pixel values, and the panoramic image pixel specific calibration functions are configured to be applied to pixel values of pixels of at least two panoramic images of the anatomy generated based on such at least two sets of detector pixel values.

16. Method according to claim 15, characterized in that the panoramic image pixel specific calibration functions are configured to, when applied to the at least two panoramic images of the anatomy, generate material decomposed panoramic images.

17. Method according to claim 16, characterized in that the panoramic image pixel specific calibration functions are configured to, when applied to the at least two panoramic images of the anatomy, compensate for X-ray beam hardening when penetrating an object.

18. Method according to claim 12, characterized in that the detector is a photon counting detector comprising pixels with at least two bins configured to detect photons of different energy ranges, and thereby to provide for a given exposure at least two sets of detector pixel values.

19. Dental panoramic imaging system, comprising:

an X-ray source (16) generating a radiation spectrum and a detector (26) comprising a two-dimensional frame of detector pixels;

a first support construction (13) configured to support the X-ray source (16) and the detector (26), wherein the first support construction (13) is configured to support the X-ray source (16) and the detector (26) at a distance from each other so as to define between them an imaging station space, and optionally a second support construction (25) designed to support an anatomy and arranged to extend within the imaging station space;

at least either of i) a driving construction configured to move the X-ray source (16) and the detector (26) in relation to the imaging station space and ii) a driving construction configured move the second support construction (25);

a data processing device, and a data communication link configured to enable the data processing device to receive information from the detector (26), wherein the dental panoramic imaging system optionally comprises a dental panoramic imaging apparatus comprising the X-ray source (16) and the detector (26) and the data processing device arranged as integrated with the apparatus;

a control system, wherein the control system comprises a first operation mode and a second operation mode and is configured to, in the first operation mode, during an imaging exposure and while information is being detected at the detector (26), cause at least one of said i) X-ray source (16) and detector (26) and ii) the second support construction (25) to move so that there will be both mutual rotational and linear movement in relation to the imaging station space, and wherein the control system is configured for both i) acquiring in the first operation mode a set of frame image data of the anatomy, which acquiring comprises using the X-ray source (16) to expose the anatomy locating within the imaging station space from different directions and detecting by the detector (26) radiation penetrating the anatomy from said different directions, and ii) acquiring in the second operation mode during a calibration exposure calibration data comprising detector pixel specific values, and wherein the data processing device is configured to generate a dental panoramic image comprising image pixel specific values by applying a frame data processing method to said set of frame image data of the anatomy, characterized in that the data processing device is configured in the second operation mode to receive calibration data relating to at least two different radiation spectra, wherein the calibration data concerning a given of said at least two radiation spectra has been acquired by using the X-ray source (16) to expose an attenuator object of known radiation attenuation characteristics and detecting by the detector (26) radiation penetrating the attenuator object, whereby an attenuator data frame of detector pixel specific values is acquired, wherein concerning acquiring a given single attenuator data frame of detector pixel specific values, the distance the radiation travels through the attenuator object when acquiring the detector pixel specific values of said attenuator data frame is known, and wherein concerning a given radiation spectrum of the at least two radiation spectra, the data processing device is configured to generate a virtual panoramic calibration image from the calibration data, wherein generating the virtual panoramic calibration image comprises multiplying said given single attenuator data frame of detector pixel specific values to constitute such set of attenuator data frames which as for the number of frames corresponds to the set of frame image data of the anatomy acquired when acquiring the set of frame image data of the anatomy and used in generating the panoramic image of the anatomy, wherein the same frame data processing method is applied to such set of attenuator data frames as the one applied to the set of frame image data acquired or to be acquired when acquiring the set of frame image data of the anatomy, and to generate panoramic image pixel specific calibration functions from the thus generated at least two virtual panoramic calibration images relating to the at least two different radiation spectra.

20. Dental panoramic imaging system according to claim 19, characterized in that the detector (26) is a detector configured to provide, regarding an individual detector pixel, at least two values based on different detecting criteria so as to provide for a given exposure at least two sets of detector pixel values, and wherein the data processing device is configured to receive at least two sets of frame image data of the anatomy based on said different detecting criteria and to generate said panoramic image of the anatomy comprising image pixel specific values, wherein said generating comprises generating at least two panoramic images of the anatomy based on said detected at least two sets of frame image data of the anatomy, and to apply the panoramic image pixel specific calibration functions to the corresponding image pixel specific values of the at least two panoramic images of the anatomy.

21. Dental panoramic imaging system according to claim 19, characterized in that the detector (26) is a photon counting detector comprising pixels with at least two bins configured to detect photons of different energy ranges, and thereby to provide for a given exposure at least two sets of detector pixel values.

22. Dental panoramic imaging system according to claim 21, characterized in that the panoramic image pixel specific calibration functions are configured to, when applied to the at least two panoramic images of the anatomy, generate material decomposed panoramic images.

23. Dental panoramic imaging system according to claim 19, characterized in that the detector (26) is a photon counting detector comprising pixels with at least two bins, the bins being configured to count photons of different energy ranges, and the data processing device is configured to use, as at least two sets of detector frame pixel specific values, sets of detector frame pixel specific values counted by the at least two bins during an exposure.

* * * * *